US011881301B2

(12) United States Patent
Gogin et al.

(10) Patent No.: US 11,881,301 B2
(45) Date of Patent: Jan. 23, 2024

(54) METHODS AND SYSTEMS FOR UTILIZING HISTOGRAM VIEWS FOR IMPROVED VISUALIZATION OF THREE-DIMENSIONAL (3D) MEDICAL IMAGES

(71) Applicant: GE Precision Healthcare LLC, Wauwatosa, WI (US)

(72) Inventors: Nicolas Gogin, Chatenay Malabry (FR); Jerome Knoplioch, Neuilly sur Seine (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 302 days.

(21) Appl. No.: 17/187,254

(22) Filed: Feb. 26, 2021

(65) Prior Publication Data
US 2022/0277834 A1    Sep. 1, 2022

(51) Int. Cl.
*G16H 30/40* (2018.01)
*G06T 11/20* (2006.01)
*G06T 7/00* (2017.01)

(52) U.S. Cl.
CPC ........... *G16H 30/40* (2018.01); *G06T 7/0012* (2013.01); *G06T 11/206* (2013.01); *G06T 2207/30061* (2013.01)

(58) Field of Classification Search
CPC ....... G06T 7/0012; G06T 11/206; G06T 5/40; G06T 5/009; G06T 2207/30096; G06T 2207/20021; G06T 2207/30061; G06T 2207/30196; G16H 30/40; G16H 50/20; G16H 10/60; G16H 70/60; G01N 33/48; A61B 5/08; A61B 5/055
See application file for complete search history.

(56) References Cited

U.S. PATENT DOCUMENTS 6,018,590 A  *  1/2000  Gaborski .................. G06T 7/12
                                                        382/209
75,962,552       5/2005  Parayil
(Continued)

OTHER PUBLICATIONS

Thamizhvani, T., Ahmed, K. T., Dhivya, A. J. A., Chandrasekaran, R., & Hemalatha, R. (2018). Analysis of MRI Slices of Hamstring Avulsion Injury using Histogram. In Journal of Clinical and Diagnostic Research. JCDR Research and Publications. https://doi.org/10.7860/jcdr/2018/36243.12362 (Year: 2018).*

(Continued)

*Primary Examiner* — Aaron W Carter
*Assistant Examiner* — Courtney Joan Nelson

(57) ABSTRACT

Systems and methods are provided for utilizing histogram views for improved visualization of three-dimensional (3D) medical images. Imaging data obtained during medical imaging examination of a patient may be processed, with the imaging data corresponding to a particular medical imaging technique. At least one medical image may be generated based on processing of the imaging data. Histogram data may be generated based on the at least one medical image. At least one histogram may be displayed along with the at least one medical image or a projection of the at least one medical image, with the at least one histogram including or being is based on the histogram data, and with the at least one histogram being displayed next to and aligned with the at least one medical image or the projection of the at least one medical image.

21 Claims, 5 Drawing Sheets

410

420

(56) References Cited

U.S. PATENT DOCUMENTS

| | | | |
|---|---|---|---|
| 8,548,215 B2* | 10/2013 | Westerhoff | G06T 7/11 324/309 |
| 2012/0126798 A1 | 5/2012 | Rondinone et al. | |
| 2014/0126798 A1* | 5/2014 | Hundley | G01R 33/283 382/131 |
| 2014/0327702 A1* | 11/2014 | Kreeger | G09G 5/377 382/131 |
| 2017/0281110 A1* | 10/2017 | Mandelkern | G06T 7/0014 |
| 2019/0096061 A1* | 3/2019 | Saito | G06T 11/206 |
| 2020/0311912 A1 | 10/2020 | Knoplioch et al. | |

OTHER PUBLICATIONS

International Search Report and Written Opinion for PCT/US2022/16533, dated Jun. 1, 2022, 8 pages.

* cited by examiner

METHODS AND SYSTEMS FOR UTILIZING HISTOGRAM VIEWS FOR IMPROVED VISUALIZATION OF THREE-DIMENSIONAL (3D) MEDICAL IMAGES

FIELD

Aspects of the present disclosure relate to medical imaging. More specifically, certain embodiments relate to methods and systems for utilizing histogram views for improved visualization of three-dimensional (3D) medical images.

BACKGROUND

Various medical imaging techniques may be used, such as in imaging organs and soft tissues in a human body. Examples of medical imaging techniques include ultrasound imaging, computed tomography (CT) scans, magnetic resonance imaging (MRI), etc. The manner by which images are generated during medical imaging depends on the particular technique.

For example, ultrasound imaging uses real time, non-invasive high frequency sound waves to produce ultrasound images, typically of organs, tissues, objects (e.g., fetus) inside the human body. Images produced or generated during medical imaging may be two-dimensional (2D), three-dimensional (3D), and/or four-dimensional (4D) images (essentially real-time/continuous 3D images). During medical imaging, imaging datasets (including, e.g., volumetric imaging datasets during 3D/4D imaging) are acquired and used in generating and rendering corresponding images (e.g., via a display) in real-time.

Use of medical imaging systems in conjunction with certain types of examination, however, poses certain challenges, particularly with respect to assessing outcome of the examination. For example, in some examinations determining presence of certain conditions or diseases by relying on detecting and/or identifying particular features in images generated and displayed in the course of the examinations, which may associated with and indicative of these conditions or diseases, may be difficult.

Further limitations and disadvantages of conventional and traditional approaches will become apparent to one of skill in the art, through comparison of such systems with some aspects of the present disclosure, as set forth in the remainder of the present application with reference to the drawings.

BRIEF SUMMARY

System and methods are provided for utilizing histogram views for improved visualization of three-dimensional (3D) medical images, substantially as shown in and/or described in connection with at least one of the figures, as set forth more completely in the claims.

These and other advantages, aspects and novel features of the present disclosure, as well as details of one or more illustrated example embodiments thereof, will be more fully understood from the following description and drawings.

DETAILED DESCRIPTION

Figure 1:
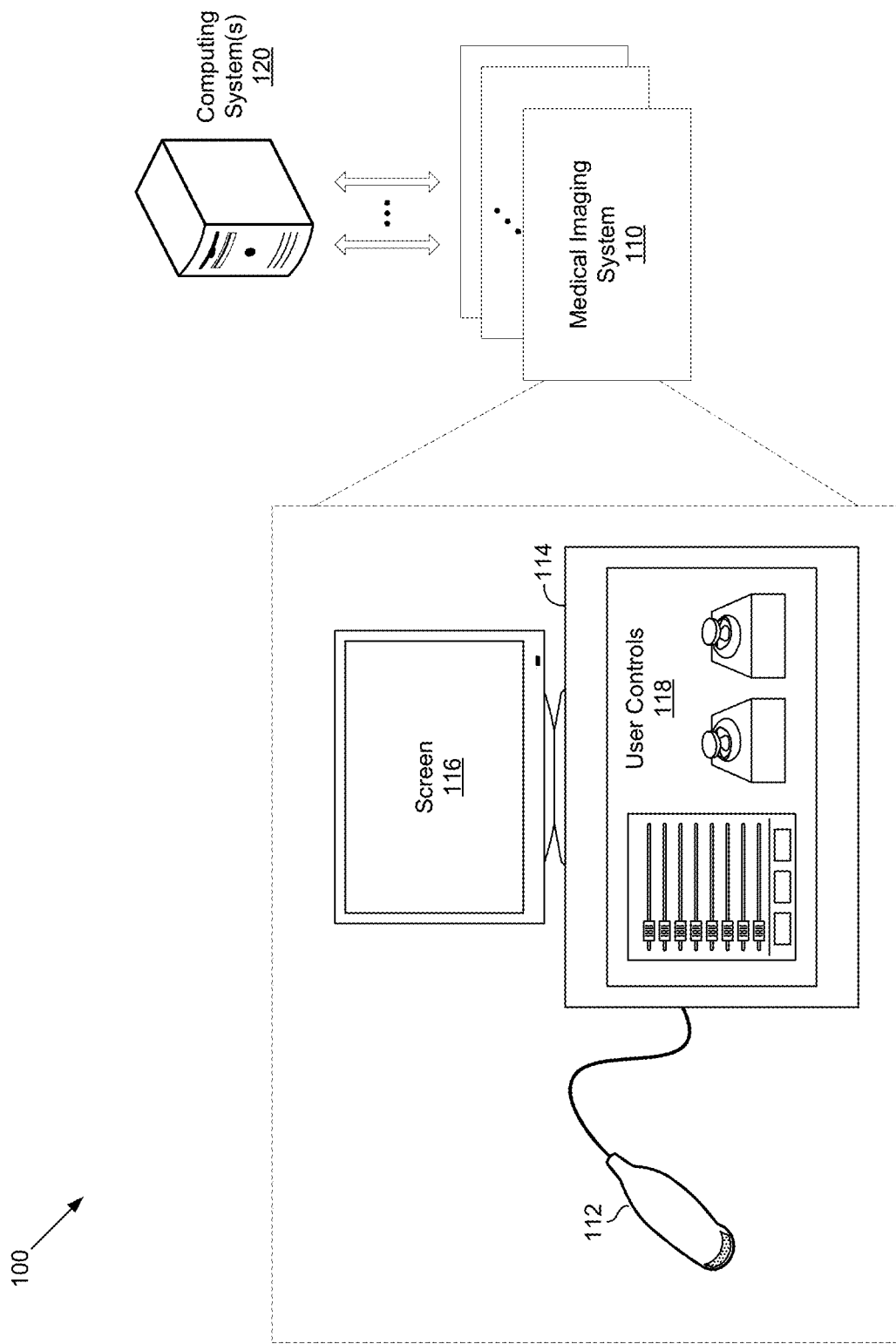
FIG. 1 is a block diagram illustrating an example medical imaging arrangement that may be configured for supporting utilizing histogram views for improved visualization of three-dimensional (3D) medical images.

Certain implementations in accordance with the present disclosure may be directed to utilizing histogram views for improved visualization of three-dimensional (3D) medical images. The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

In addition, as used herein, the phrase "pixel" also includes embodiments where the data is represented by a "voxel." Thus, both the terms "pixel" and "voxel" may be used interchangeably throughout this document.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC, or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". In addition, forming of images may be performed using channel combinations that may originate from more than one transmit event (e.g., synthetic aperture techniques).

Figure 2:
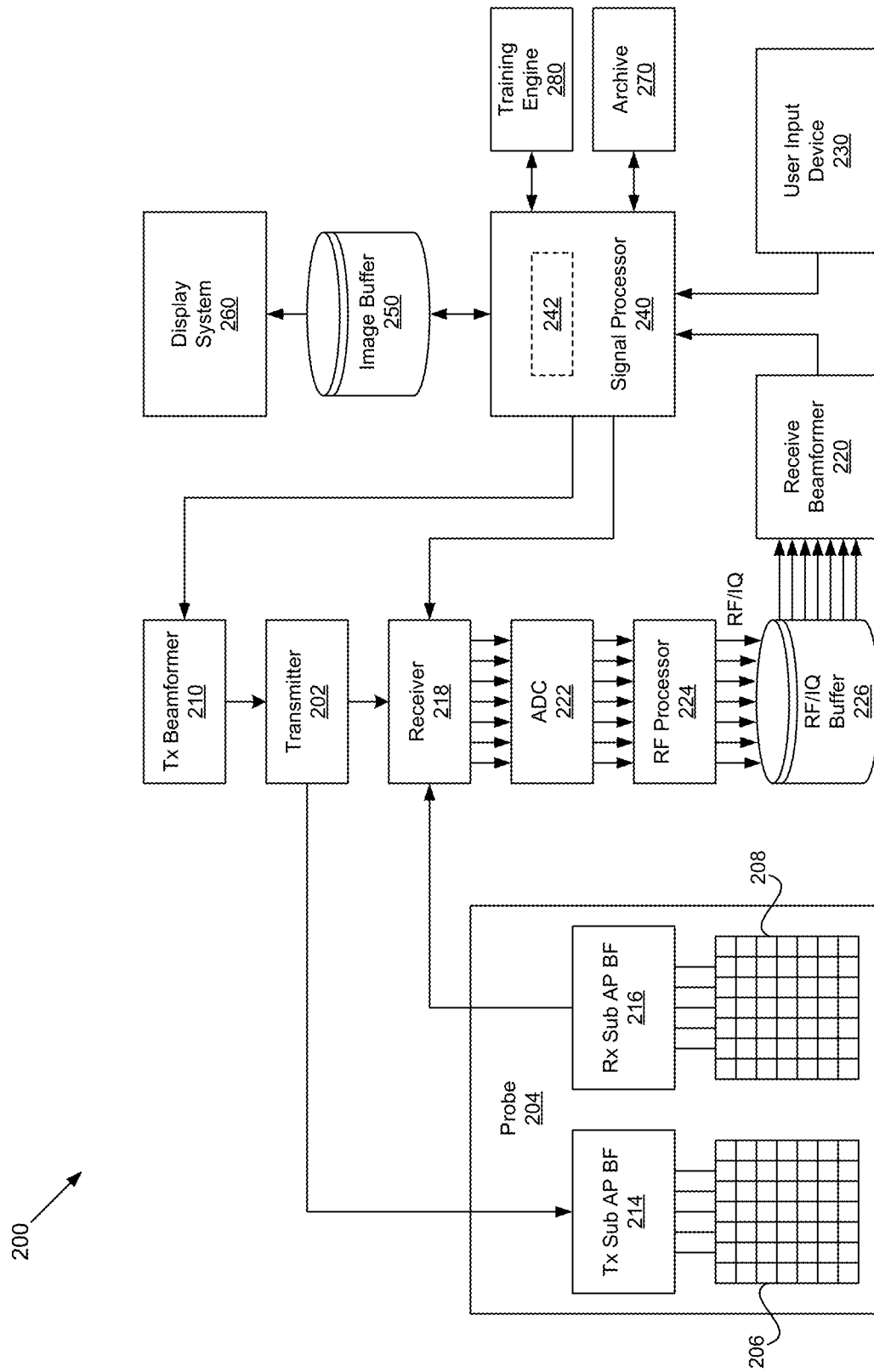
FIG. 2 is a block diagram illustrating an example ultrasound system that may be configured for supporting utilizing histogram views for improved visualization of three-dimensional (3D) medical images.

In various embodiments, processing to form images, including beamforming, is performed in software, firmware, hardware, or a combination thereof. One example implementation of an ultrasound system having a software beamformer architecture formed in accordance with various embodiments as illustrated in FIG. 2.

FIG. 1 is a block diagram illustrating an example medical imaging arrangement that may be configured for supporting utilizing histogram views for improved visualization of three-dimensional (3D) medical images. Shown in FIG. 1 is an example setup 100 that comprises one or more medical imaging systems 110 and one or more computing systems 120.

The medical imaging system 110 comprise suitable hardware, software, or a combination thereof, for supporting medical imaging—that is enabling obtaining data used in generating and/or rendering images during medical imaging exams. Examples of medical imaging include ultrasound imaging, computed tomography (CT) scans, magnetic resonance imaging (MRI), etc. This may entail capturing of particular type of data, in particular manner, which may in turn be used in generating data for the images. For example, the medical imaging system 110 may be an ultrasound imaging system, configured for generating and/or rendering ultrasound images. An example implementation of an ultrasound system, which may correspond to the medical imaging system 110, is described in more detail with respect to FIG. 2.

As shown in FIG. 1, the medical imaging system 110 may comprise a scanner device 112, which may be portable and movable, and a display/control unit 114. The scanner device 112 may be configured for generating and/or capturing particular type of imaging signals (and/or data corresponding thereto), such as by being moved over a patient's body (or part thereof), and may comprise suitable circuitry for performing and/or supporting such functions. The scanner device 112 may be an ultrasound probe, MRI scanner, CT scanner, or any suitable imaging device. For example, where the medical imaging system 110 is an ultrasound system, the scanner device 112 may emit ultrasound signals and capture echo ultrasound images.

The display/control unit 114 may be configured for displaying images (e.g., via a screen 116). In some instances, the display/control unit 114 may further be configured for generating the displayed images, at least partly. Further, the display/control unit 114 may also support user input/output. For example, the display/control unit 114 may provide (e.g., via the screen 116), in addition to the images, user feedback (e.g., information relating to the system, functions thereof, settings thereof, etc.). The display/control unit 114 may also support user input (e.g., via user controls 118), such as to allow controlling of the medical imaging. The user input may be directed to controlling display of images, selecting settings, specifying user preferences, requesting feedback, etc.

In some implementation, the medical imaging system 110 may also incorporate additional and dedicated computing resources, such as the one or more computing systems 120. In this regard, each computing system 120 may comprise suitable circuitry, interfaces, logic, and/or code for processing, storing, and/or communication data. The computing system 120 may be dedicated equipment configured particularly for use in conjunction with medical imaging, or it may be a general purpose computing system (e.g., personal computer, server, etc.) set up and/or configured to perform the operations described hereinafter with respect to the computing system 120. The computing system 120 may be configured to support operations of the medical imaging systems 110, as described below. In this regard, various functions and/or operations may be offloaded from the imaging systems. This may be done to streamline and/or centralize certain aspects of the processing, to reduce cost—e.g., by obviating the need to increase processing resources in the imaging systems.

The computing systems 120 may be set up and/or arranged for use in different ways. For example, in some implementations a single computing system 120 may be used; in other implementations multiple computing systems 120, either configured to work together (e.g., based on distributed-processing configuration), or separately, with each computing system 120 being configured to handle particular aspects and/or functions, and/or to process data only for particular medical imaging systems 110. Further, in some implementations, the computing systems 120 may be local (e.g., co-located with one or more medical imaging systems 110, such within the same facility and/or same local network); in other implementations, the computing systems 120 may be remote and thus can only be accessed via remote connections (e.g., via the Internet or other available remote access techniques). In a particular implementation, the computing systems 120 may be configured in cloud-based manner, and may be accessed and/or used in substantially similar way that other cloud-based systems are accessed and used.

Once data is generated and/or configured in the computing system 120, the data may be copied and/or loaded into the medical imaging systems 110. This may be done in different ways. For example, the data may be loaded via directed connections or links between the medical imaging systems 110 and the computing system 120. In this regard, communications between the different elements in the setup 100 may be done using available wired and/or wireless connections, and/or in accordance any suitable communication (and/or networking) standards or protocols. Alternatively, or additionally, the data may be loaded into the medical imaging systems 110 indirectly. For example, the data may be stored into suitable machine readable media (e.g., flash card, etc.), which are then used to load the data into the medical imaging systems 110 (on-site, such as by users of the systems (e.g., imaging clinicians) or authorized personnel), or the data may be downloaded into local communication-capable electronic devices (e.g., laptops, etc.), which are then used on-site (e.g., by users of the systems or authorized personnel) to upload the data into the medical imaging systems 110, via direct connections (e.g., USB connector, etc.).

In operation, the medical imaging system 110 may be used in generating and presenting (e.g., rendering or displaying) images during medical exams, and/or in supporting user input/output in conjunction therewith. The images may be 2D, 3D, and/or 4D images. The particular operations or functions performed in the medical imaging system 110 to facilitate the generating and/or presenting of images depends on the type of system—that is, the manner by which the data corresponding to the images is obtained and/or generated. For example, in ultrasound imaging, the data is based on emitted and echo ultrasound signals, as described in more detail with respect to FIG. 2.

In various implementations, medical imaging systems (e.g., the medical imaging system 110) may be configured to support utilizing histogram views for improved visualization of three-dimensional (3D) medical images. In this regard, in some instances it may be desirable to improve medical imaging by providing enhanced visualization features that may make review of medical images, particularly 3D images, easier and more convenient for those performing the medical imaging based examination. In particular, review and analysis of 3D medical images during medical imaging examinations is may be a tedious task.

For example, in many instances review and analysis of 3D medical images may involve review of multiple two-dimensional (2D) images—e.g., native image slices of the volume, reformatted 2D images, 3D projection images (e.g., MIP), or volume rendering. The workflow may be interactive because the information of a 3D volume cannot be displayed through a single image or limited number of images. The use of projection images (e.g., maximum intensity projection, volume rendering, etc.) may often be used to provide a summary view of an organ (e.g., lungs, heart, liver, vessels etc.) that allows the radiologist to quickly identify suspicious areas or features, and to navigate through the stack of images towards those areas. However, those projection images give a partial representation of the 3D volume, which in some cases may impair correct interpretation, e.g., of certain features in the images.

Accordingly, enhanced visualization features may be used to improve medical imaging, particularly 3D images. Use of such visualization features may be particularly useful and advantageous when examining certain organs and/or when the imaging is done to check for particular conditions. This may be done, for example, by incorporating use of histograms, which may provide information (e.g., visually) that allow for identifying areas or features (or enhancing thereof) requiring special and added attention more easily and readily. This is described in more detail below.

For example, the histograms may be generated and displayed during medical imaging. In particular, this may be done by generating and displaying histogram(s) along with the corresponding medical images (e.g., CT images, MR images, etc.), or projection thereof, particularly in manner that would enhance medical examination—e.g., aligned to the medical image, to allow for enhanced comparison, which may allow for improved detection of areas or features of interest within the image, which may require additional and careful examination. In some instances, the histogram(s) may be positioned, for example, beside the image and/or may share a common axis therewith. Thus, in various implementations, one-dimensional (1D) histogram(s) are generated and displayed, aligned to 2D projection view of 3D images (sharing same axis). Bars of each histogram may be oriented in pre-determined manner (e.g., based on the common axis), which may be determined as optimize detection of pertinent features.

In some example implementations, dual histogram views may be used, particularly where use of such dual views may be advantageous or beneficial, such as for enhanced side-by-side comparison. In this regard, a dual histogram view may be generated and displayed, aligned to an image or a projection thereof (e.g., CT image, MR image, etc.), such as to facilitate side-by-side (e.g., left-right) comparison. The histograms may be positioned on, for example, either side of a projection from a 3D image and share a common axis (e.g., z-axis) therewith, with bars of each histogram oriented symmetrically relative to the common axis. Use of such dual histograms may be useful for improving medical imaging based examination of particular organs, such as the lungs (e.g., using CT lung imaging), to enhanced left-right comparisons, where one histogram may be used for the left lung, the other one for the right lung. Use of dual histogram views in this manner may improve medical examination of the lungs, particularly in conjunction with certain respiratory diseases, such as the coronavirus disease 2019 (COVID-19), for which bilateral distribution of lesions is known to be an important biomarker.

User of histogram(s) in accordance with the present disclosure may allow for addressing some of the issues with conventional solutions, particularly by ensuring and/or enhancing correct interpretation of pertinent features in the images. In this regard, use of 1D histograms along with the 3D projection provides additional information to the user that can indicate more clearly the suspicious areas, while providing quantifiable volumetric information. For example, in the case of lung disease, the histogram views may be used to show the distribution of high attenuation areas, such as along the axis aligned to an average intensity projection. In this regard, the 3D projection indicates the localization of the high attenuation areas within the lungs, in the x,z-plane, while the histogram view provides additional information on the extent of the area taking into account also the extent along the y-axis. Examples of use of histogram views in conjunction with medical imaging examination of the lungs are shown and described in more detail below, with respect to FIGS. 3 and 4.

In various implementations, the histograms, or information used and provided therein, may be generated based the medical images or data corresponding thereto. For example, during medical imaging, imaging datasets (including, e.g., volumetric imaging datasets for 3D/4D imaging) may be acquired in the medical imaging systems and then used (within the medical imaging systems or in other systems, local or remote) in generating and rendering corresponding images (e.g., via a display). Thus, the information used in the histograms may be obtained or generated based on processing of the imaging datasets and/or data obtained therefrom (e.g., for use in generating and displaying the corresponding images).

Further, in some implementations the displaying the histograms and/or the generating of information used in the histograms may be done locally (directly within the medical imaging system or a local system) or remotely (in the Cloud, remote data center, etc.). This may allow for use of histograms in distributed manner—e.g., with data used in generating the histogram being done in one location, the processing to generate the histograms or data used therein being done in another location, and the displaying of the histogram (and the corresponding images) being done in yet another location.

FIG. 2 is a block diagram illustrating an example ultrasound system that may be configured for supporting utilizing histogram views for improved visualization of three-dimensional (3D) medical images. Shown in FIG. 2 is an ultrasound system 200.

The ultrasound system 200 may be configured for providing ultrasound imaging, and as such may comprise suitable circuitry, interfaces, logic, and/or code for performing and/or supporting ultrasound imaging related functions. The ultrasound system 200 may correspond to the medical imaging system 110 of FIG. 1. The ultrasound system 200 comprises, for example, a transmitter 202, an ultrasound probe 204, a transmit beamformer 210, a receiver 218, a receive beamformer 220, a RF processor 224, a RF/IQ buffer 226, a user input module 230, a signal processor 240, an image buffer 250, a display system 260, an archive 270, and a training engine 280.

The transmitter 202 may comprise suitable circuitry, interfaces, logic, and/or code that may be operable to drive an ultrasound probe 204. The ultrasound probe 204 may comprise a two dimensional (2D) array of piezoelectric elements. The ultrasound probe 204 may comprise a group of transmit transducer elements 206 and a group of receive transducer elements 208, that normally constitute the same elements. In certain embodiment, the ultrasound probe 204 may be operable to acquire ultrasound image data covering at least a substantial portion of an anatomy, such as the heart, a blood vessel, or any suitable anatomical structure.

The transmit beamformer 210 may comprise suitable circuitry, interfaces, logic, and/or code that may be operable to control the transmitter 202 which, through a transmit sub-aperture beamformer 214, drives the group of transmit transducer elements 206 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 208.

The group of receive transducer elements 208 in the ultrasound probe 204 may be operable to convert the received echoes into analog signals, undergo sub-aperture beamforming by a receive sub-aperture beamformer 216 and are then communicated to a receiver 218. The receiver 218 may comprise suitable circuitry, interfaces, logic, and/or code that may be operable to receive the signals from the receive sub-aperture beamformer 216. The analog signals may be communicated to one or more of the plurality of A/D converters 222.

The plurality of A/D converters 222 may comprise suitable circuitry, interfaces, logic, and/or code that may be operable to convert the analog signals from the receiver 218 to corresponding digital signals. The plurality of A/D converters 222 are disposed between the receiver 218 and the RF processor 224. Notwithstanding, the disclosure is not limited in this regard. Accordingly, in some embodiments, the plurality of A/D converters 222 may be integrated within the receiver 218.

The RF processor 224 may comprise suitable circuitry, interfaces, logic, and/or code that may be operable to demodulate the digital signals output by the plurality of A/D converters 222. In accordance with an embodiment, the RF processor 224 may comprise a complex demodulator (not shown) that is operable to demodulate the digital signals to form I/Q data pairs that are representative of the corresponding echo signals. The RF or I/Q signal data may then be communicated to an RF/IQ buffer 226. The RF/IQ buffer 226 may comprise suitable circuitry, interfaces, logic, and/or code that may be operable to provide temporary storage of the RF or I/Q signal data, which is generated by the RF processor 224.

The receive beamformer 220 may comprise suitable circuitry, interfaces, logic, and/or code that may be operable to perform digital beamforming processing to, for example, sum the delayed channel signals received from RF processor 224 via the RF/IQ buffer 226 and output a beam summed signal. The resulting processed information may be the beam summed signal that is output from the receive beamformer 220 and communicated to the signal processor 240. In accordance with some embodiments, the receiver 218, the plurality of A/D converters 222, the RF processor 224, and the beamformer 220 may be integrated into a single beamformer, which may be digital. In various embodiments, the ultrasound system 200 comprises a plurality of receive beamformers 220.

The user input device 230 may be utilized to input patient data, scan parameters, settings, select protocols and/or templates, interact with an artificial intelligence segmentation processor to select tracking targets, and the like. In an example embodiment, the user input device 230 may be operable to configure, manage and/or control operation of one or more components and/or modules in the ultrasound system 200. In this regard, the user input device 230 may be operable to configure, manage and/or control operation of the transmitter 202, the ultrasound probe 204, the transmit beamformer 210, the receiver 218, the receive beamformer 220, the RF processor 224, the RF/IQ buffer 226, the user input device 230, the signal processor 240, the image buffer 250, the display system 260, and/or the archive 270.

For example, the user input device 230 may include button(s), rotary encoder(s), a touchscreen, motion tracking, voice recognition, a mouse device, keyboard, camera and/or any other device capable of receiving user directive(s). In certain embodiments, one or more of the user input devices 230 may be integrated into other components, such as the display system 260 or the ultrasound probe 204, for example.

As an example, user input device 230 may include a touchscreen display. As another example, user input device 230 may include an accelerometer, gyroscope, and/or magnetometer attached to and/or integrated with the probe 204 to provide gesture motion recognition of the probe 204, such as to identify one or more probe compressions against a patient body, a pre-defined probe movement or tilt operation, or the like. In some instances, the user input device 230 may include, additionally or alternatively, image analysis processing to identify probe gestures by analyzing acquired image data. In accordance with the present disclosure, the user input and functions related thereto may be configured to support use of histogram views. For example, users may be able to, via the user input device 230, request histogram views, indicate where or how to display the histogram views, and/or set or adjust parameters relating to the histogram views and display thereof.

The signal processor 240 may comprise suitable circuitry, interfaces, logic, and/or code that may be operable to process ultrasound scan data (i.e., summed IQ signal) for generating ultrasound images for presentation on a display system 260. The signal processor 240 is operable to perform one or more processing operations according to a plurality of selectable ultrasound modalities on the acquired ultrasound scan data. In an example embodiment, the signal processor 240 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 226 during a scanning session and processed in less than real-time in a live or off-line operation. In various embodiments, the processed image data can be presented at the display system 260 and/or may be stored at the archive 270. The archive 270 may be a local archive, a Picture Archiving and Communication System (PACS), or any suitable device for storing images and related information.

The signal processor 240 may be one or more central processing units, microprocessors, microcontrollers, and/or the like. The signal processor 240 may be an integrated component, or may be distributed across various locations, for example. The signal processor 240 may be configured for receiving input information from the user input device 230 and/or the archive 270, generating an output displayable by the display system 260, and manipulating the output in response to input information from the user input device 230, among other things. The signal processor 240 may be capable of executing any of the method(s) and/or set(s) of instructions discussed herein in accordance with the various embodiments, for example.

The ultrasound system 200 may be operable to continuously acquire ultrasound scan data at a frame rate that is suitable for the imaging situation in question. Typical frame rates range from 20-220 but may be lower or higher. The acquired ultrasound scan data may be displayed on the display system 260 at a display-rate that can be the same as the frame rate, or slower or faster. The image buffer 250 is included for storing processed frames of acquired ultrasound scan data that are not scheduled to be displayed immediately. Preferably, the image buffer 250 is of sufficient capacity to store at least several minutes' worth of frames of ultrasound scan data. The frames of ultrasound scan data are stored in a manner to facilitate retrieval thereof according to its order or time of acquisition. The image buffer 250 may be embodied as any known data storage medium.

In an example embodiment, the signal processor 240 may comprise a histogram viewing module 242, which comprises suitable circuitry, interfaces, logic, and/or code that may be configured to perform and/or support various functions or operations relating to, or in support of utilizing histogram views for improved visualization of three-dimensional (3D) medical images, as described in this disclosure.

In some implementations, the signal processor 240 (and/or components thereof, such as the histogram viewing module 242) may be configured to implement and/or use artificial intelligence and/or machine learning techniques to enhance and/or optimize imaging related functions or operations. For example, the signal processor 240 (and/or components thereof, such as the histogram viewing module 242) may be configured to implement and/or use deep learning techniques and/or algorithms, such as by use of deep neural networks (e.g., a convolutional neural network (CNN)), and/or may utilize any suitable form of artificial intelligence image analysis techniques or machine learning processing functionality, which may be configured to analyze acquired ultrasound images, such as to identify, segment, label, and track structures (or tissues thereof) meeting particular criteria and/or having particular characteristics.

In an example implementation, the signal processor 240 (and/or components thereof, such as the histogram viewing module 242) may be provided as a deep neural network, which may be made up of, for example, an input layer, an output layer, and one or more hidden layers in between the input and output layers. Each of the layers may be made up of a plurality of processing nodes that may be referred to as neurons. For example, the deep neural network may include an input layer having a neuron for each pixel or a group of pixels from a scan plane of an anatomical structure, and the output layer may have a neuron corresponding to a plurality of pre-defined structures or types of structures (or tissue(s) therein). Each neuron of each layer may perform a processing function and pass the processed ultrasound image information to one of a plurality of neurons of a downstream layer for further processing.

As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The neurons of a fourth layer may learn characteristics of particular tissue types present in particular structures, etc. Thus, the processing performed by the deep neural network (e.g., convolutional neural network (CNN)) may allow for identifying biological and/or artificial structures in ultrasound image data with a high degree of probability.

In some implementations, the signal processor 240 (and/or components thereof, such as the histogram viewing module 242) may be configured to perform or otherwise control at least some of the functions performed thereby based on a user instruction via the user input device 230. As an example, a user may provide a voice command, probe gesture, button depression, or the like to issue a particular instruction, such as to initiate and/or control various aspects of use of histogram views for enhanced visualizing of medical imaging, including artificial intelligence (AI) based analysis of the images or data corresponding thereto (for use in the histogram views and generating and/or displaying thereof), and/or to provide or otherwise specify various parameters or settings relating thereto, as described in this disclosure.

The training engine 280 may comprise suitable circuitry, interfaces, logic, and/or code that may be operable to train the neurons of the deep neural network(s) of the signal processor 240 (and/or components thereof, such as the histogram viewing module 242). For example, the signal processor 240 may be trained to identify particular structures and/or tissues (or types thereof) provided in an ultrasound scan plane, with the training engine 280 training the deep neural network(s) thereof to perform some of the required functions, such as using databases(s) of classified ultrasound images of various structures.

As an example, the training engine 280 may be configured to utilize ultrasound images of particular structures to train the signal processor 240 (and/or components thereof, such as the histogram viewing module 242) with respect to the characteristics of the particular structure(s), such as the appearance of structure edges, the appearance of structure shapes based on the edges, the positions of the shapes relative to landmarks in the ultrasound image data, and the like, and/or with respect to characteristics of particular tissues (e.g., softness thereof). In various embodiments, the databases of training images may be stored in the archive 270 or any suitable data storage medium. In certain embodiments, the training engine 280 and/or training image databases may be external system(s) communicatively coupled via a wired or wireless connection to the ultrasound system 200.

In operation, the ultrasound system 200 may be used in generating ultrasonic images, including two-dimensional (2D), three-dimensional (3D), and/or four-dimensional (4D) images. In this regard, the ultrasound system 200 may be operable to continuously acquire ultrasound scan data at a particular frame rate, which may be suitable for the imaging situation in question. For example, frame rates may range from 20-70 but may be lower or higher. The acquired ultrasound scan data may be displayed on the display system 260 at a display-rate that can be the same as the frame rate, or slower or faster. An image buffer 250 is included for storing processed frames of acquired ultrasound scan data not scheduled to be displayed immediately. Preferably, the image buffer 250 is of sufficient capacity to store at least several seconds' worth of frames of ultrasound scan data. The frames of ultrasound scan data are stored in a manner to facilitate retrieval thereof according to its order or time of acquisition. The image buffer 250 may be embodied as any known data storage medium.

In some instances, the ultrasound system 200 may be configured to support grayscale and color based operations. For example, the signal processor 240 may be operable to perform grayscale B-mode processing and/or color processing. The grayscale B-mode processing may comprise processing B-mode RF signal data or IQ data pairs. For example, the grayscale B-mode processing may enable forming an envelope of the beam-summed receive signal by computing the quantity $(I^2+Q^2)^{1/2}$. The envelope can undergo additional B-mode processing, such as logarithmic compression to form the display data.

The display data may be converted to X-Y format for video display. The scan-converted frames can be mapped to grayscale for display. The B-mode frames that are provided to the image buffer 250 and/or the display system 260. The color processing may comprise processing color based RF signal data or IQ data pairs to form frames to overlay on B-mode frames that are provided to the image buffer 250 and/or the display system 260. The grayscale and/or color processing may be adaptively adjusted based on user input—e.g., a selection from the user input device 230, for example, for enhance of grayscale and/or color of particular area.

In some instances, ultrasound imaging may include generation and/or display of volumetric ultrasound images—that is where objects (e.g., organs, tissues, etc.) are displayed three-dimensional 3D. In this regard, with 3D (and similarly 4D) imaging, volumetric ultrasound datasets may be acquired, comprising voxels that correspond to the imaged objects. This may be done, e.g., by transmitting the sound waves at different angles rather than simply transmitting them in one direction (e.g., straight down), and then capture their reflections back. The returning echoes (of transmissions at different angles) are then captured, and processed (e.g., via the signal processor 240) to generate the corresponding volumetric datasets, which may in turn be used in creating and/or displaying volume (e.g. 3D) images, such as via the display 250. This may entail use of particular handling techniques to provide the desired 3D perception.

For example, volume rendering techniques may be used in displaying projections (e.g., 2D projections) of the volumetric (e.g., 3D) datasets. In this regard, rendering a 2D projection of a 3D dataset may comprise setting or defining a perception angle in space relative to the object being displayed, and then defining or computing necessary information (e.g., opacity and color) for every voxel in the dataset. This may be done, for example, using suitable transfer functions for defining RGBA (red, green, blue, and alpha) value for every voxel.

In various implementations, the ultrasound system 200 may be configured to support utilizing histogram views for improved visualization of three-dimensional (3D) medical images, as described in this disclosure. In this regard, as noted above, histogram views may be used to improve medical imaging based examinations, by incorporating display of histogram views that include information that would allow users to identify and detect areas or features in the images, which may correspond to particular conditions or diseases, more quickly and easily.

For example, during ultrasound imaging operation in the ultrasound system 200, histograms may be displayed via the display system 260 along with the corresponding images, particularly in manner that would enhance medical examination—e.g., with the histogram(s) aligned to the medical image, to allow for enhanced detection of areas or features of interest within the images. In some instances, dual histograms may be used, such when imaging dual organs (e.g., the lungs), for enhanced left-right comparisons, as described above.

The data used in the histogram may be generated based on the acquired ultrasound scan data or data obtained based processing thereof (e.g., for image display via the display system 260). In this regard, in some instances the histogram data may be obtained or generated directly within the ultrasound system 200 (e.g., in the signal processor 240 and/or components thereof, such as the histogram viewing module 242); alternatively, the histogram data may be obtained or generated in a separate system (e.g., a local or remote system), which may receive data from the ultrasound system (e.g., the acquired ultrasound scan data or data obtained based processing thereof) and send back the histogram data based on processing of the received data. Use of separate systems for providing the histogram data may be desirable—e.g., to avoid using resources in the medical imaging system, to allow making updates or revisions to histogram viewing related functions more efficient (as it would reduce the number of systems that need to be updated), etc.

Once histogram data is obtained or generated, the histogram may be displayed. In this regard, the histogram views may be displayed in a manner that optimized detection—e.g., beside and aligned with the images. For example, one-dimensional (1D) histogram(s) may be displayed aligned to 2D projection view of 3D images (sharing same axis). Examples of histograms are shown and described in more detail below, with respect to FIGS. 3 and 4.

Figure 3:
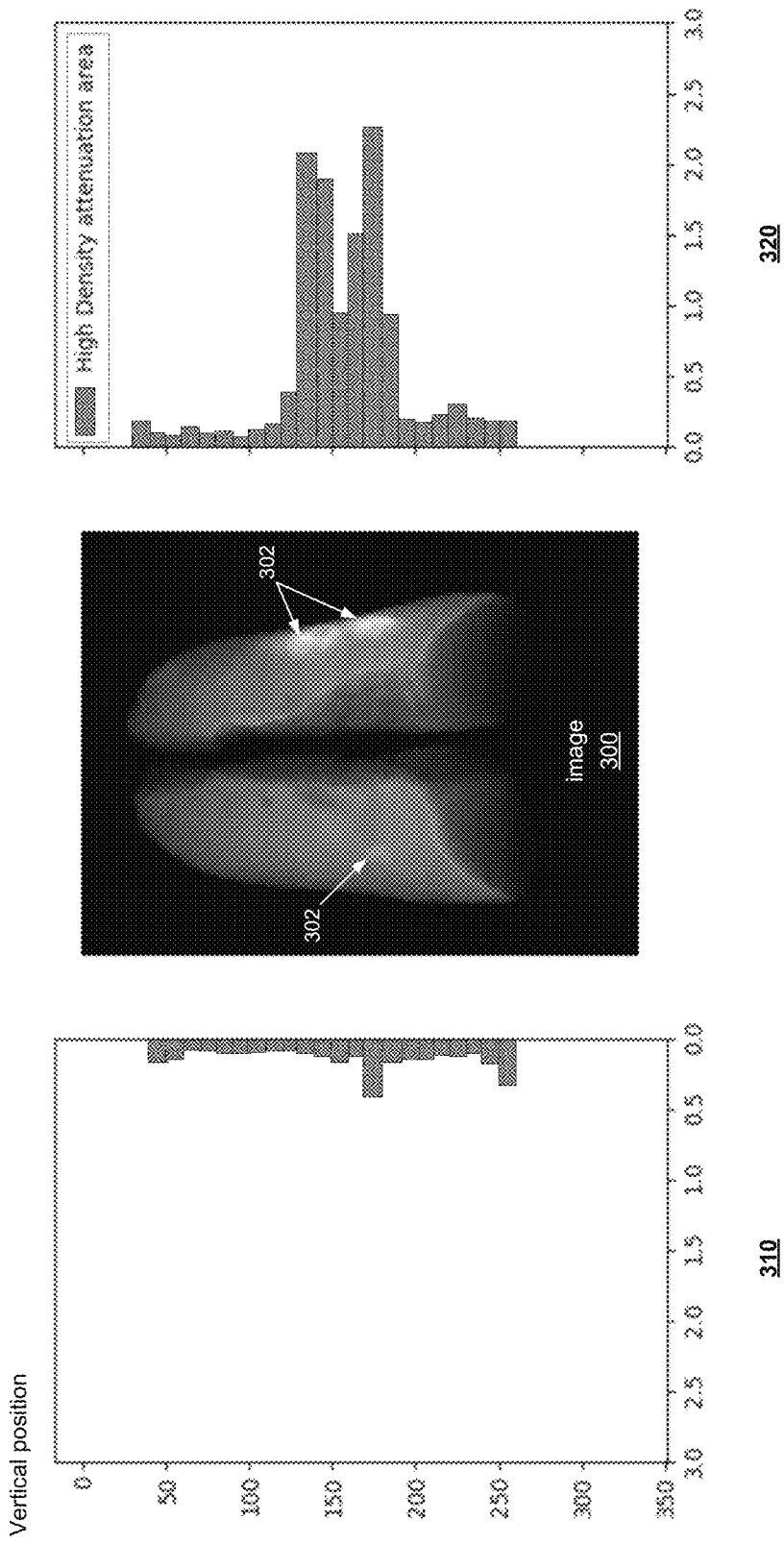
FIG. 3 illustrates an example use scenario of an example medical imaging system configured for supporting histograms, with histograms generated and displayed along with projections of medical images.

FIG. 3 illustrates an example use scenario of an example medical imaging system configured for supporting histograms, with histograms generated and displayed along with projections of medical images. Shown in FIG. 3 is a screenshot of a medical image 300 along with corresponding one-dimensional (1D) histograms 310 and 320.

The medical image 300 may be generated and displayed in an example medical imaging system (e.g., the medical imaging system 100 of FIG. 1) during medical imaging examination. In particular, as shown in FIG. 3, the medical image 300 may be a two-dimensional (2D) projection view (e.g., average intensity projection) based on a three-dimensional (3D) volume. In the example use scenario illustrated in FIG. 3, the medical image 300 is an image of lungs.

In accordance with an example implementation of the present disclosure, the one-dimensional (1D) histograms 310 and 320 may be generated and displayed, being aligned with and either side of the medical image 300. In this regard, as noted above, use of histograms may be advantageous, particularly in conjunction with certain medical imaging exams, such as when examining lungs. Displaying the 1D histograms 310 and 320 in this manner may be desirable in certain situations, such for enhancing left-right comparisons. Such enhanced left-right comparisons may be desirable during examination of the lungs, for example.

Each of the histograms 310 and 320 comprises a plurality of bins, corresponding to slices within the organ(s) being examined (e.g., the left and right lungs, respectively), with width of each bin corresponding to a particular range. In this regard, in each of the histograms 310 and 320 values along the y-axis correspond to vertical positions within the lungs, whereas the values on x-axis corresponds to metric values for each bin. Thus, as shown in FIG. 3, the histograms 310 and 320 include metrics (e.g., high density attenuation) averaged along x-y axis for each of the bins, with each bin corresponding to a slice through the lung at the vertical position indicated on the y-axis. As illustrated in FIG. 3, the use of histograms 310 and 320 helps to identify and quantify quickly certain features in the lungs, such as hyper-dense lesion(s), corresponding to regions 302 in the medical image 300.

In some implementations, some of the parameters relating to the histograms (e.g., width of the bins) may be configurable or adjustable by the user. However, the parameters and configuration of histogram should be maintained constant when comparing images (e.g., images corresponding to different patients, images for the same patient but at different times, etc.).

Figure 4:
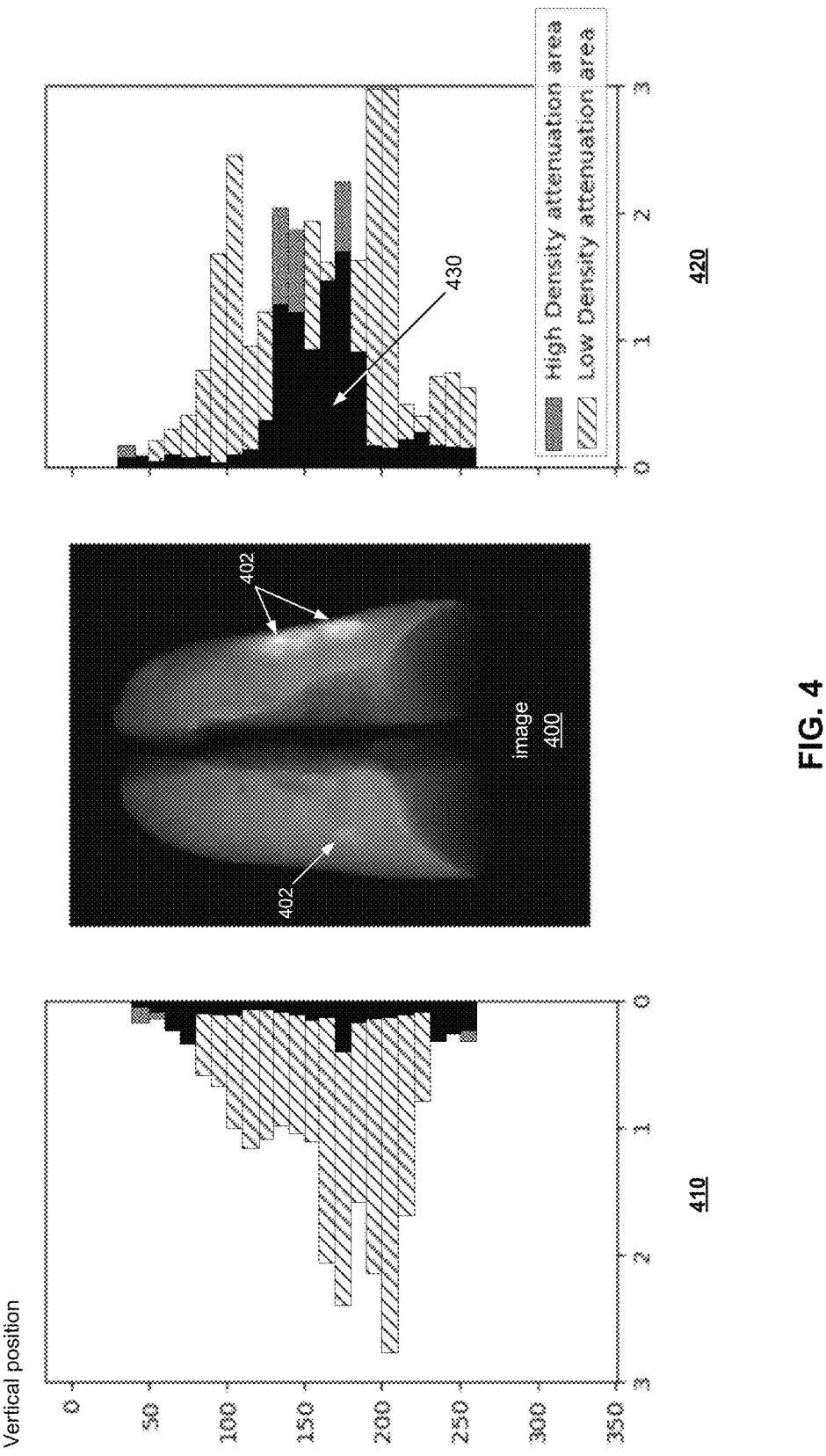
FIG. 4 illustrates an example use scenario of an example medical imaging system configured for supporting histograms, with histograms incorporating with multiple metrics generated and displayed along with projections of medical images.

FIG. 4 illustrates an example use scenario of an example medical imaging system configured for supporting histograms, with histograms incorporating with multiple metrics generated and displayed along with projections of medical images. Shown in FIG. 4 is a screenshot of a medical image 400 along with corresponding one-dimensional (1D) histograms 410 and 420.

The medical image 400 may be generated and displayed in an example medical imaging system (e.g., the medical imaging system 100 of FIG. 1) during medical imaging examination. In particular, as shown in FIG. 4, the medical image 400 may be a two-dimensional (2D) projection view (e.g., average intensity projection) based on a three-dimensional (3D) volume. In the example use scenario illustrated in FIG. 4, the medical image 400 is an image of lungs.

The one-dimensional (1D) histograms 410 and 420 may be generated and displayed, aligned with and either side of the medical image 400, for enhanced left-right comparison, which may be desirable, e.g., during examination of the lungs. The histograms 410 and 420 may be similar to the histograms 310 and 320, and thus similarly may include metrics averaged along x-y axis, for each slice in each of the histograms 410 and 420. The histograms 410 and 420 may include multiple metrics, however.

In this regard, the histograms 410 and 420 may comprise a plurality of bins, with width of each bin corresponding to a particular range (e.g., z-axis based range [z1,z2]). The height of each bar within each bin may be determined based on some metric computed on this slice range. Example of metrics may comprise area/volume (mm2 or mm3) of a segmentation, ratio of area between 2 segmentation masks, voxel value statistics (mean, std, texture, etc.), and the like.

As illustrated in the example use scenario shown in FIG. 4, in some implementations, the histograms (e.g., histograms 410 and 420 in FIG. 4) may be generated based on, and such show multiple metrics (e.g., high density attenuation and low density attenuation), which may be superimposed within at least some of the bins/slices. The disclosure is not so limitation, however, and other types of histograms may be used, such as stacked histograms, where the different metrics may be stacked on top of each other.

Use of multiple metrics in conjunction with use of dual histogram view—that is, within dual histograms, with each histogram displayed symmetrically on each part or side of the image—maybe particularly desirable for bilateral organs (e.g., lungs, kidneys, brain (left/right structures thereof), bones, lymph nodes, etc.). In this regard, use of dual histogram view in conjunction with use of multiple superimposed metrics may further enhance and improve identifying and quantifying certain features, such as hyper-dense lesion(s) in the lungs (e.g., corresponding to regions 402 in the medical image 400) as it may further emphasize bilateral extent of lesions in the lungs. This maybe particularly useful when using medical imaging to check for conditions typical of certain respiratory diseases, such as the coronavirus disease 2019 (COVID-19).

Figure 5:
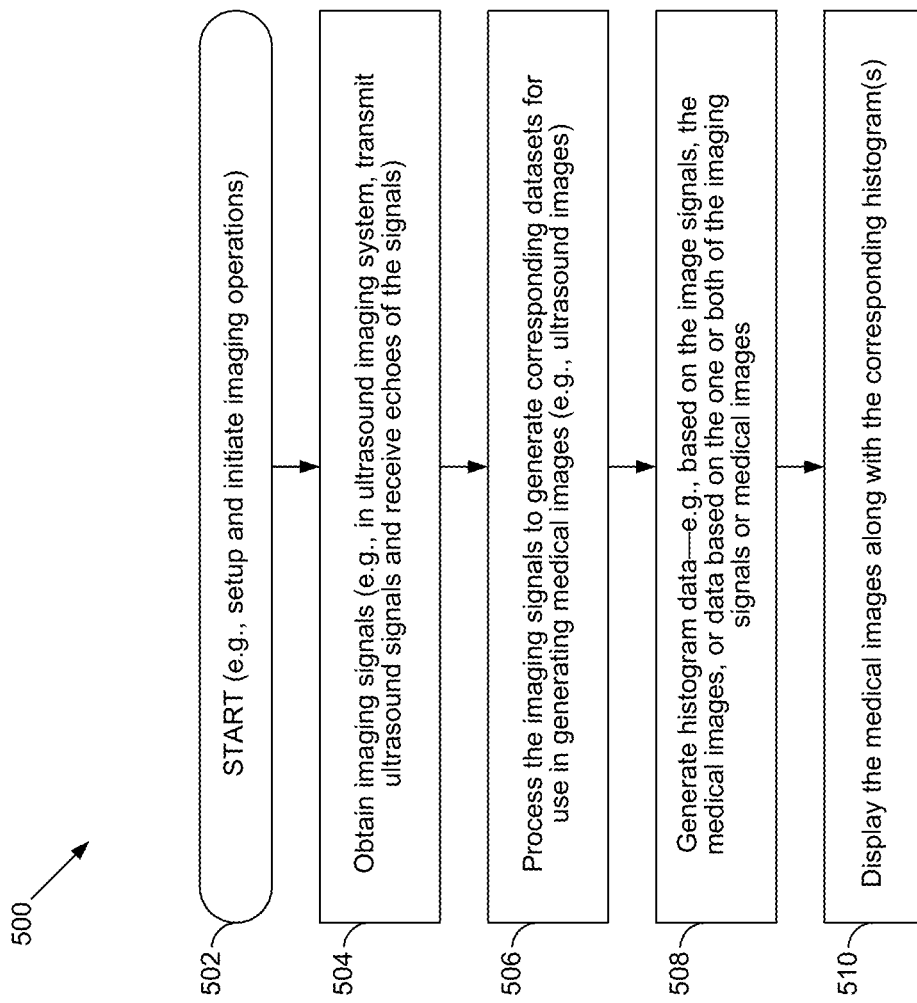
FIG. 5 illustrates a flowchart of an example process for using histogram views for improved visualization of medical images.

FIG. 5 illustrates a flowchart of an example process for using histogram views for improved visualization of medical images. Shown in FIG. 5 is flow chart 500, comprising a plurality of example steps (represented as blocks 502-510), which may be performed in a suitable medical imaging system (e.g., the medical imaging system 110 of FIG. 1 or the ultrasound system 200 of FIG. 2) for using histogram views for improved visualization of medical images.

In start step 502, the system may be setup, and operations may initiate.

In step 504, imaging signals may be obtained during a medical imaging based examination (e.g., of lungs). For example, in an ultrasound imaging system (e.g., the ultrasound system 200 of FIG. 2), this may comprise transmitting ultrasound signals and receiving corresponding echoes of the signals.

In step 506, the imaging signals (e.g., received echoes of the ultrasound signals) may be processed (e.g., via the display/control unit 114 of the medical imaging system 110, or the signal processor 240 of the ultrasound system 200), to generate corresponding datasets for use in generating corresponding medical images (e.g., ultrasound images). In this regard, the medical images may be three-dimensional (3D) images.

In step 508, histogram data may be generated. In this regard, as described above, the histograms or information used therein may be generated based on, e.g., the image signals, the medical images, or data based on the one or both of the imaging signals or medical images (e.g., via processing thereof, such as via the display/control unit 114 of the medical imaging system 110, or the signal processor 240 and the histogram viewing module 242 of the ultrasound system 200). Further, as described above, the generating of histogram data may be done within the medical imaging system or in another system (local or remote).

In step 510, the medical images may be displayed along with the corresponding histogram(s). For example, as illustrated in FIGS. 3 and 4, one-dimensional (1D) histogram view(s) may be displayed (e.g., via the display system 260 of the ultrasound system 200), such as along (e.g., beside and aligned with) two-dimensional (2D) projections of the 3D images. In some instances, the information may be transmitted, such as to a remote device (e.g., for displaying therein). Also, in some instances, an alert or some other suitable indication may be generated and provided in lieu of or in conjunction with the displaying of the information.

An example method, in accordance with the present disclosure, comprises processing imaging data obtained during medical imaging examination of a patient, wherein the imaging data corresponds to a particular medical imaging technique; generating at least one medical image based on processing of the imaging data; generating histogram data based on the at least one medical image; and displaying at least one histogram along with the at least one medical image or a projection of the at least one medical image, wherein: the at least one histogram comprises or is based on the histogram data; and the at least one histogram is displayed next to and aligned with the at least one medical image or the projection of the at least one medical image.

In an example implementation, the method further comprises displaying two histograms along with the at least one medical image or the projection of the at least one medical image, wherein: the two histograms are displayed on either of two opposites sides of the at least one medical image or the projection of the at least one medical image.

In an example implementation, the generating the histogram data comprises determining values for at least one metric for a plurality of slices within the at least one medical image.

In an example implementation, the method further comprises determining values for two or more metrics for the plurality of slices within the at least one medical image, and wherein: displaying the at least one histogram comprises displaying the values of the two or more metrics within the at least one histogram.

In an example implementation, the method further comprises displaying the values of the two or more metrics within the at least one histogram as superimposed or stacked values.

In an example implementation, the method further comprises offloading generating at least a portion of the histogram data, or at least a portion of processing for the generating of the at least portion of the histogram data.

In an example implementation, the method further comprises setting or adjusting the displaying of the at least one histogram based on user input.

An example non-transitory computer readable medium, in accordance with the present disclosure, may have stored thereon it a computer program having at least one code section, the at least one code section being executable by a machine comprising at least one processor, for causing the machine to perform one or more steps comprising processing imaging data obtained during medical imaging examination of a patient, wherein the imaging data corresponds to a particular medical imaging technique; generating at least one medical image based on processing of the imaging data; generating histogram data based on the at least one medical image; and displaying at least one histogram along with the at least one medical image or a projection of the at least one medical image, wherein: the at least one histogram comprises or is based on the histogram data; and the at least one histogram is displayed next to and aligned with the at least one medical image or the projection of the at least one medical image.

In an example embodiment, the one or more steps further comprise displaying two histograms along with the at least one medical image or the projection of the at least one medical image, wherein: the two histograms are displayed on either of two opposites sides of the at least one medical image or the projection of the at least one medical image.

In an example embodiment, the generating the histogram data comprises determining values for at least one metric for a plurality of slices within the at least one medical image.

In an example embodiment, the one or more steps further comprise determining values for two or more metrics for the plurality of slices within the at least one medical image, and wherein: displaying the at least one histogram comprises displaying the values of the two or more metrics within the at least one histogram.

In an example embodiment, the one or more steps further comprise displaying the values of the two or more metrics within the at least one histogram as superimposed or stacked values.

In an example embodiment, the one or more steps further comprise offloading generating at least a portion of the histogram data, or at least a portion of processing for the generating of the at least portion of the histogram data.

In an example embodiment, the one or more steps further comprise setting or adjusting the displaying of the at least one histogram based on user input.

An example system, in accordance with the present disclosure, comprises a device configured to obtaining imaging data during medical imaging examination of a patient, wherein the imaging data corresponds to a particular medical imaging technique; a display device configured to display medical images; and at least one processor configured to: process the imaging data obtained during the medical imaging examination; generate at least one medical image based on processing of the imaging data; generate histogram data based on the at least one medical image; and display, via the display device, at least one histogram along with the at least one medical image or a projection of the at least one medical image, wherein: the at least one histogram comprises or is based on the histogram data; and the at least one histogram is displayed next to and aligned with the at least one medical image or the projection of the at least one medical image.

In an example embodiment, the at least one processor is configured to display, via the display device, two histograms along with the at least one medical image or the projection of the at least one medical image, wherein: the two histograms are displayed on either of two opposites sides of the at least one medical image or the projection of the at least one medical image.

In an example embodiment, the at least one processor is configured to, when generating the histogram data, determine values for at least one metric for a plurality of slices within the at least one medical image.

In an example embodiment, the at least one processor is configured to determine values for two or more metrics for the plurality of slices within the at least one medical image, and wherein: displaying the at least one histogram comprises displaying the values of the two or more metrics within the at least one histogram.

In an example embodiment, the at least one processor is configured to display the values of the two or more metrics within the at least one histogram as superimposed or stacked values.

In an example embodiment, the at least one processor is configured to offloading generating at least a portion of the histogram data, or at least a portion of processing for the generating of the at least portion of the histogram data.

In an example embodiment, the at least one processor is configured to set or adjust the displaying of the at least one histogram based on user input.

As utilized herein the terms "circuits" and "circuitry" refer to physical electronic components (e.g., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z." As utilized herein, the terms "block" and "module" refer to functions than can be performed by one or more circuits. As utilized herein, the term "exemplary" means serving as a non-limiting example, instance, or illustration. As utilized herein, the terms "for example" and "e.g.," set off lists of one or more non-limiting examples, instances, or illustrations. As utilized herein, circuitry is "operable" to perform a function whenever the circuitry comprises the necessary hardware (and code, if any is necessary) to perform the function, regardless of whether performance of the function is disabled or not enabled (e.g., by some user-configurable setting, a factory trim, etc.).

Other embodiments of the invention may provide a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the processes as described herein.

Accordingly, the present disclosure may be realized in hardware, software, or a combination of hardware and software. The present invention may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip.

Various embodiments in accordance with the present disclosure may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method comprising:
processing imaging data obtained during medical imaging examination of a patient, wherein the imaging data correspond to a particular medical imaging technique;
generating at least one medical image based on processing of the imaging data;
determining values for two or more metrics for the plurality of slices within the at least one medical image;
generating histogram data with a plurality of bins corresponding to said slices, based on the at least one medical image; and
displaying one of the at least one medical image in the center of a display, one histogram to the left side of the one medical image on the display and corresponding to medical data on the left side of the medical image, and a second histogram to the right side of the one medical image and corresponding to medical data on the right side of the medical image, wherein:
the two histograms comprise or are based on the histogram data;
the two histograms are displayed next to and aligned with each other and the at least one medical image; and
displaying at least one of the histograms includes displaying the values of the two or more metrics within the histogram as superimposed or stacked values.

2. The method of claim 1, further comprising offloading generating at least a portion of the histogram data, or at least a portion of processing for the generating of the at least portion of the histogram data.

3. The method of claim 1, further comprising setting or adjusting the displaying of at least one of the histograms based on user input.

4. The method of claim 1, wherein imaging data includes lung image data and at least one of the metrics relates to COVID-19 disease.

5. The method of claim 1, wherein the metrics include at least one of area divided by volume of a segmentation, ratio between two segmentation masks, voxel value statistics, high density attenuation, or low density attenuation.

6. The method of claim 1, wherein the medical image shows a bilateral organ.

7. The method of claim 1, wherein the histograms are aligned to the medical image on the display such that the values displayed related to the plurality of slices are aligned horizontally with the section of the image containing the corresponding slices.

8. A non-transitory computer readable medium having stored thereon a computer program having at least one code section, the at least one code section being executable by a machine comprising at least one processor, for causing the machine to perform one or more steps comprising:
processing imaging data obtained during medical imaging examination of a patient, wherein the imaging data correspond to a particular medical imaging technique;
generating at least one medical image based on processing of the imaging data;
determining values for two or more metrics for the plurality of slices within the at least one medical image;
generating histogram data with a plurality of bins corresponding to said slices, based on the at least one medical image; and displaying one of the at least one medical image in the center of a display, one histogram to the left side of the one medical image on the display and corresponding to medical data on the left side of the medical image, and a second histogram to the right side of the one medical image and corresponding to medical data on the right side of the medical image, wherein:
the two histograms comprise or are based on the histogram data;
the two histograms are displayed next to and aligned with each other and the at least one medical image; and
displaying at least one of the histograms includes displaying the values of the two or more metrics within the histogram as superimposed or stacked values.

9. The non-transitory computer readable medium of claim 8, wherein the one or more steps further comprise offloading generating at least a portion of the histogram data, or at least a portion of processing for the generating of the at least portion of the histogram data.

10. The non-transitory computer readable medium of claim 8, wherein the one or more steps further comprise setting or adjusting the displaying of at least one histogram based on user input.

11. The non-transitory computer readable medium of claim 8, wherein imaging data includes lung image data and at least one of the metrics relates to COVID-19 disease.

12. The non-transitory computer readable medium of claim 8, wherein the metrics include at least one of area divided by volume of a segmentation, ratio between two segmentation masks, voxel value statistics, high density attenuation, or low density attenuation.

13. The non-transitory computer readable medium of claim 8, wherein the medical image shows a bilateral organ.

14. The non-transitory computer readable medium of claim 8, wherein the histograms are aligned to the medical image on the display such that the values displayed related to the plurality of slices are aligned horizontally with the section of the image containing the corresponding slices.

15. A system comprising:
a device configured to obtain imaging data during medical imaging examination of a patient, wherein the imaging data correspond to a particular medical imaging technique;
a display device configured to display medical images; and
at least one processor configured to:
process the imaging data obtained during the medical imaging examination;
generate at least one medical image based on processing of the imaging data;
determine values for two or more metrics for the plurality of slices within the at least one medical image;
generating histogram data with a plurality of bins corresponding to said slices, based on the at least one medical image; and
display, via the display device, one of the at least one medical image in the center of a display, one histogram to the left side of the one medical image on the display and corresponding to medical data on the left side of the medical image, and a second histogram to the right side of the one medical image and corresponding to medical data on the right side of the medical image, wherein:
the two histograms comprise or are based on the histogram data;
the two histograms are displayed next to and aligned with each other and the at least one medical image; and
displaying at least one of the histograms includes displaying the values of the two or more metrics within the histogram as superimposed or stacked values.

16. The system of claim 15, wherein the at least one processor is configured to offload generating at least a portion of the histogram data, or at least a portion of processing for the generating of the at least portion of the histogram data.

17. The system of claim 15, wherein the at least one processor is configured to set or adjust the displaying of at least one histogram based on user input.

18. The system of claim 15, wherein imaging data includes lung image data and at least one of the metrics relates to COVID-19 disease.

19. The system of claim 15, wherein the metrics include at least one of area divided by volume of a segmentation, ratio between two segmentation masks, voxel value statistics, high density attenuation, or low density attenuation.

20. The system of claim 15, wherein the medical image shows a bilateral organ.

21. The system of claim 15, wherein the histograms are aligned to the medical image on the display such that the values displayed related to the plurality of slices are aligned horizontally with the section of the image containing the corresponding slices.

* * * * *